United States Patent
Fischer

(10) Patent No.: US 7,922,487 B2
(45) Date of Patent: *Apr. 12, 2011

(54) CHEMICALLY PRE-IMPREGNATED SILK RETRACTION CORDS HAVING INCREASED STRENGTH

(75) Inventor: Dan E. Fischer, Sandy, UT (US)

(73) Assignee: Ultradent Products, Inc., South Jordan, UT (US)

( * ) Notice: Subject to any disclaimer, the term of this patent is extended or adjusted under 35 U.S.C. 154(b) by 144 days.

This patent is subject to a terminal disclaimer.

(21) Appl. No.: 12/135,756

(22) Filed: Jun. 9, 2008

(65) Prior Publication Data

US 2009/0305188 A1    Dec. 10, 2009

(51) Int. Cl.
*A61C 5/14* (2006.01)
(52) U.S. Cl. .................................. 433/136
(58) Field of Classification Search .......... 433/136, 433/138, 139, 215
See application file for complete search history.

(56) References Cited

U.S. PATENT DOCUMENTS

| | | | |
|---|---|---|---|
| 4,321,038 A * | 3/1982 | Porteous | 433/136 |
| 4,465,462 A | 8/1984 | Ticknor | |
| 4,522,593 A | 6/1985 | Fischer | |
| 4,617,950 A | 10/1986 | Porteous et al. | |
| 4,728,291 A | 3/1988 | Golub | |
| 4,871,311 A | 10/1989 | Hagne | |
| 4,892,482 A | 1/1990 | Lococo | |
| 5,022,859 A | 6/1991 | Oliva | |
| 5,540,588 A | 7/1996 | Earle | |
| 5,558,652 A | 9/1996 | Henke | |
| 5,676,543 A | 10/1997 | Dragan | |
| 5,874,164 A | 2/1999 | Caldwell | |
| 5,899,694 A | 5/1999 | Summer | |
| 6,179,872 B1 | 1/2001 | Bell et al. | |
| 6,375,461 B1 | 4/2002 | Jensen et al. | |
| 6,455,030 B2 | 9/2002 | Saito et al. | |
| 6,612,839 B2 | 9/2003 | Loynes | |
| 7,121,828 B2 | 10/2006 | Fischer et al. | |
| 7,168,951 B2 | 1/2007 | Fischer et al. | |

(Continued)

FOREIGN PATENT DOCUMENTS

JP    1139057    5/1989

(Continued)

OTHER PUBLICATIONS

Cotton retrieved from http:swicofil.com/products/OOIcotton.html.*

(Continued)

*Primary Examiner* — Cris L Rodriguez
*Assistant Examiner* — Eric Rosen
(74) *Attorney, Agent, or Firm* — Workman Nydegger

(57) ABSTRACT

A degradation resistant gingival retraction cord including silk is formed from two or more strands that are braided, twisted or woven. The degradation resistant retraction cord comprises at least about 50% silk, 80% silk, 90% silk, 95% silk, or essentially all silk. They are able to maintain at least about 70%, 80% or 90% of this tensile strength for a time period of at least about 7 days, 30 days, 60 days, or 90 days. The silk retraction cords have the look, feel and desirable utility of a thin, flexible, and resilient natural fiber cord, while also resisting degradation when pre-impregnated with a corrosive agent. Such cords combine the degradation resistance of a man-made fiber, while also having greater liquid absorbance, lightness, flexibility and resilience like a natural fiber cord.

32 Claims, 4 Drawing Sheets

U.S. PATENT DOCUMENTS

| | | | | |
|---|---|---|---|---|
| 2002/0081550 | A1* | 6/2002 | Karazivan | 433/80 |
| 2005/0277087 | A1 | 12/2005 | Fischer et al. | |
| 2005/0277088 | A1 | 12/2005 | Fischer et al. | |
| 2006/0060819 | A1 | 3/2006 | Jung | |
| 2007/0111160 | A1 | 5/2007 | Fischer et al. | |
| 2008/0096164 | A1 | 4/2008 | Fischer | |
| 2009/0098501 | A1* | 4/2009 | Klettke et al. | 433/8 |

FOREIGN PATENT DOCUMENTS

| | | |
|---|---|---|
| JP | 06056833 | 3/2006 |
| WO | WO2005/122945 | 12/2005 |

OTHER PUBLICATIONS

Selecting the Right Fiber for the Right Product by Kim Anderson. Retrieved from http:llwww.techexchange.comlthelibrarylselecting.html.*

History of Silk retrieved from http://weyouth.wordpress.com/2007/09/14/history-of-silk/.*

Office Action dated Jan. 13, 2009 cited in U.S. Appl. No. 11/551,542.

Goswami et al., Textile Yarns, Technology, Structure and Applications: John Wiley & Sons 1997, pp. 26-27.

Office Action dated Sep. 14, 2007 cited in related U.S. Appl. No. 11/551,542.

Final Office Action dated Feb. 26, 2008 cited in related U.S. Appl. No. 11/551,542.

Office Action dated Jul. 14, 2008 cited in related U.S. Appl. No. 11/551,542.

Braid. (n.d.). The American Heritage® Dictionary of the English Language, Fourth Edition. Retrieved Feb. 19, 2008, from Dictionary.com website: http://dictionary.reference.com/browse/braid.

Fazekas, A., "Effects of Pre-Soaked Retraction Cords on the Microcirculation of the Human Gingival Margin" Oper Dent 27(4): 343-8 2002.

Neito-Martinez, D., "Effects of Diameter, Chemical Impregnation and Hydration on the Tensile Strength of Gingival Retraction Cords" J. Oral Rehibil, 28(12): 1094-100 2002.

O'Mahony, A., "Effect of 3 Medicaments on the Dimensional Accuracy and Surface Detail Reproduction of Polyvinyl Siloxane Impressions" Quintessential Int., 31(3): 201-6 2001.

Donovan, T.E., "Review and Survey of Medicaments Used With Gingival Retraction Cords" J. Prosthet Dent, 53(4): 525-31 1985.

Office Action dated Feb. 8, 2006 cited in U.S. Appl. No. 11/064,725.

Office Action dated May 10, 2006 cited in U.S. Appl. No. 11/064,725.

Office Action dated Jul. 17, 2006 cited in U.S. Appl. No. 11/064,725.

NOA dated Dec. 1, 2006 cited in U.S. Appl. No. 11/064,725.

Office Action dated Feb. 8, 2006 cited in U.S. Appl. No. 10/863,974.

Office Action dated May 10, 2006 cited in U.S. Appl. No. 10/863,974.

NOA dated Jul. 20, 2006 cited in U.S. Appl. No. 10/863,974.

Office Action dated Aug. 4, 2010 cited in U.S. Appl. No. 11/622,844.

Notice of Allowance dated Oct. 14, 2010 cited in U.S. Appl. No. 11/622,844.

Goswami et al., Textile Yarns Technology, Structure and Applications, John Wiley & Sons (1977), pp. 26-27.

Office Action dated Aug. 14, 2009 cited in U.S. Appl. No. 11/622,844.

Office Action dated May 12, 2010 cited in U.S. Appl. No. 11/622,844.

Office Action dated Nov. 4, 2009 cited in related U.S. Appl. No. 11/551,542.

Office Action dated Jun. 14, 2010 cited in related U.S. Appl. No. 11/551,542.

Notice of Allowance dated Nov. 15, 2010 cited in U.S. Appl. No. 11/551,542.

* cited by examiner

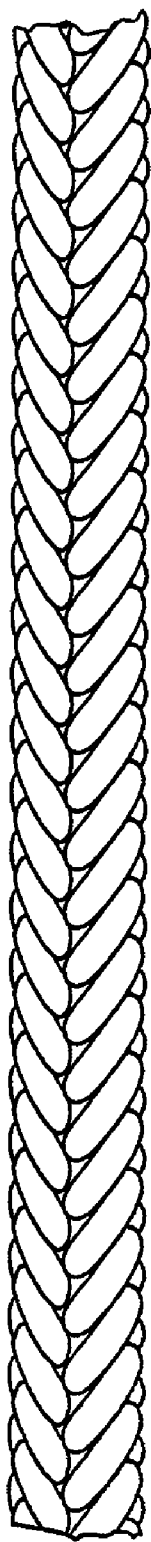 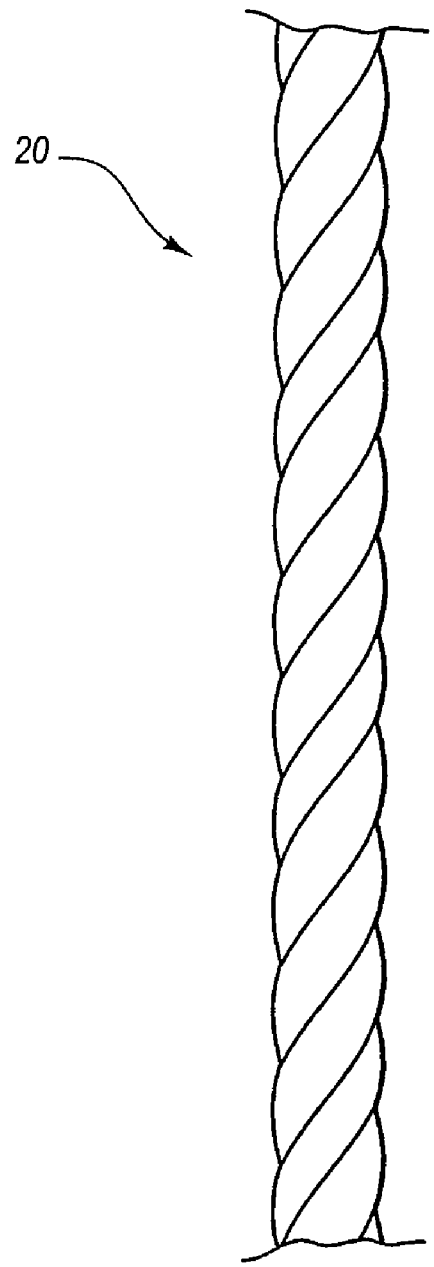
FIG. 1A  FIG. 1B

CHEMICALLY PRE-IMPREGNATED SILK RETRACTION CORDS HAVING INCREASED STRENGTH

BACKGROUND OF THE INVENTION

1. The Field of the Invention

The present invention relates to gingival retraction cords. More particularly, the present invention relates to chemically pre-impregnated silk retraction cords having high resistance to degradation over time.

2. The Related Technology

When performing various dental procedures, it is often desirable to retract the gingival tissue to prepare the patient's teeth for the procedure (e.g., to take an accurate and reliable impression of the tooth). Taking dental impressions, placing crowns, performing bridge work, or effecting other dental restorations are examples of procedures that benefit from retracted gingival tissue. A widely used method for retracting gingival tissue involves the use of retraction cords which are typically braided or knitted for increased strength, flexibility and resilience. Examples of gingival retraction cords may be found in U.S. Pat. No. 4,321,038 to Porteous, U.S. Pat. No. 4,522,593 to Fischer, U.S. Pat. No. 4,617,950 to Porteous et al., U.S. Pat. No. 4,892,482 to Lococo, U.S. Pat. No. 7,121,828 to Fischer et al., and U.S. Pub. No. 2008/0096164, which are incorporated herein by reference.

In addition to making it more difficult to take an accurate impression of the proper shape of a patient's tooth beneath the gingival margin, the gingiva (or "gums") can also bleed if torn or damaged by a high speed cutting drill or burr used to remove tooth material preparatory to placing a crown. Bleeding may further interfere with taking a good impression because extravasated blood can prevent adequate cleaning and drying of the marginal area of the tooth prior to taking an impression and displace the impression material before it can set. Thus, the dual problems of contraction of the gingival cuff and the presence of hemorrhaging tissues make it impractical to simply take an impression following shaping of the tooth with a high speed drill or burr without retraction of the gingiva.

To control or inhibit gingival bleeding, retraction cords can be treated with a hemostatic agent. One type of hemostatic agent includes an astringent, which lock or seal off exposed blood vessels so as to arrest bleeding. U.S. Pat. Nos. 4,321,038, 4,522,593, 4,617,950 and 4,892,482, referred to above, discuss the use of astringents such as potassium aluminum sulfate, also known as "alum". More powerful astringents include iron based salts, which are highly acidic and corrosive.

Highly acidic chemicals used to impregnate a retraction cord can adversely affect the strength and integrity of the retraction cord. Retraction cords are typically made of natural fibers, such as cotton, which are highly absorbent and can absorb and retain high quantities of a liquid astringent. However, applying a corrosive hemostatic agent to a retraction cord made of natural fibers such as cotton or other cellulose based fibers can quickly degrade the cord and reduce its strength and integrity, making it more likely to fray and/or fail during use. If fibers in the retraction cord fail during use, the dental packing instrument used to insert the retraction cord into the sulcus can slip through the fibers and potentially cut or injure the underlying tissue. In addition, fragments of the retraction cord can remain embedded between the tooth and gums, providing greater risk of infection. Frayed filaments can easily lodge within coagulum, which can be painful to the patient and result in a recurrence of bleeding when the cord is removed. Furthermore, the expandability and resilience of the retraction cord diminishes as the integrity of the knit or weave of the cord degrades.

In view of the foregoing, gingival retraction cords made from absorbent natural fibers such as cotton or other cellulose based fibers cannot be feasibly pre-impregnated with corrosive agents, such as iron based hemostatic agents, and then shipped in bulk to end users. Doing so would yield a cord that is so friable and weak as to be useless as a retraction cord. Instead, corrosive agents have been applied to natural fiber retraction cords by the dental practitioner chair side, just prior to use.

Man-made fibers, such as nylon and polyester, can be used to make gingival retraction cords that resist degradation by corrosive agents. However, cords made from man-made fibers are bulkier and far less absorbent than retraction cords made from natural fibers, such as cotton. As a result, such cords are less desirable than natural fiber cords.

BRIEF SUMMARY OF THE INVENTION

The present invention is directed to gingival retraction cords made using degradation resistant natural fibers so as to have the look, feel and desirable utility of a thin, flexible, and resilient natural fiber cord, while also resisting degradation when pre-impregnated with a corrosive agent. Such cords are able to combine the degradation resistance of a man-made fiber, while also having greater liquid absorbance, lightness, flexibility and resilience like a natural fiber cord. This surprising and unexpected combination of features is obtained by manufacturing a retraction cord primarily or exclusively from silk fibers.

Silk retraction cords according to the invention can be pre-impregnated with a corrosive agent, such as an acidic iron-based hemostatic salt, and then packaged and shipped to end users without a substantial loss of strength and resilience. Embodiments of pre-impregnated silk retraction cords according to the invention are able to maintain at least about 70% of their tensile strength over a time period of at least about 7 days, preferably at least about 30 days, more preferably at least about 60 days, and most preferably at least about 90 days.

According to one embodiment, the invention provides a pre-packaged, chemically impregnated gingival retraction cord that is resistant to degradation by corrosive agents over time, comprising: (1) a gingival retraction cord comprising two or more strands that are joined together so as to be deformable and liquid absorbent, wherein the retraction cord comprises at least about 50% silk; (2) a corrosive agent impregnated within the retraction cord, wherein the retraction cord resists degradation by the active agent so as to maintain at least about 70% of its tensile strength over a time period of at least about 7 days; and (3) a moisture-resistant packaging container within which the retraction cord is stored prior to use.

The chemically impregnated gingival retraction cord preferably comprises at least about 80% silk, more preferably at least about 90% silk, and most preferably at least about 95% silk. According to one embodiment, the retraction cord consists essentially of silk and is substantially free of man-made fibers such as nylon and polyester. The strands used to make the retraction cord may comprise or consist essentially of silk fibers and may be joined together in one of several known ways, such as braiding, twisting or weaving. If woven, the weave can be rolled up and/or twisted to form an elongated strand.

The chemical agent impregnated within the gingival retraction cord can be applied as a liquid, such as an active agent that is dissolved or dispersed in a solvent. According to one embodiment, the solvent is a non-volatile liquid in order for the pre-impregnated gingival retraction cord to remain wet over time. Alternatively, the solvent can be a volatile liquid, such as an alcohol, ketone and/or water, which can be removed by evaporation in order to convert the active agent into a dried residue. In the case of cotton fibers, drying a retraction cord that has been impregnated with a liquid corrosive hemostatic agent can exacerbate degradation of the cotton cord. In contrast, retraction cords that are primarily or exclusive comprised of silk are substantially resistant to degradation over time, even after drying.

These and other advantages and features of the present invention will become more fully apparent from the following description and appended claims, or may be learned by the practice of the invention as set forth hereinafter.

BRIEF DESCRIPTION OF DRAWINGS

To further clarify the above and other advantages and features of the present invention, a more particular description of the invention will be rendered by reference to specific embodiments thereof which are illustrated in the appended drawings. It is appreciated that these drawings depict only illustrated embodiments of the invention and are therefore not to be considered limiting of its scope. The invention will be described and explained with additional specificity and detail through the use of the accompanying drawings in which:

FIG. 1A illustrates an exemplary silk-containing retraction cord having multiple knitted strands;

FIG. 1B illustrates an exemplary silk-containing retraction cord having multiple twisted strands;

DETAILED DESCRIPTION OF EXEMPLARY EMBODIMENTS

Figure 1C:
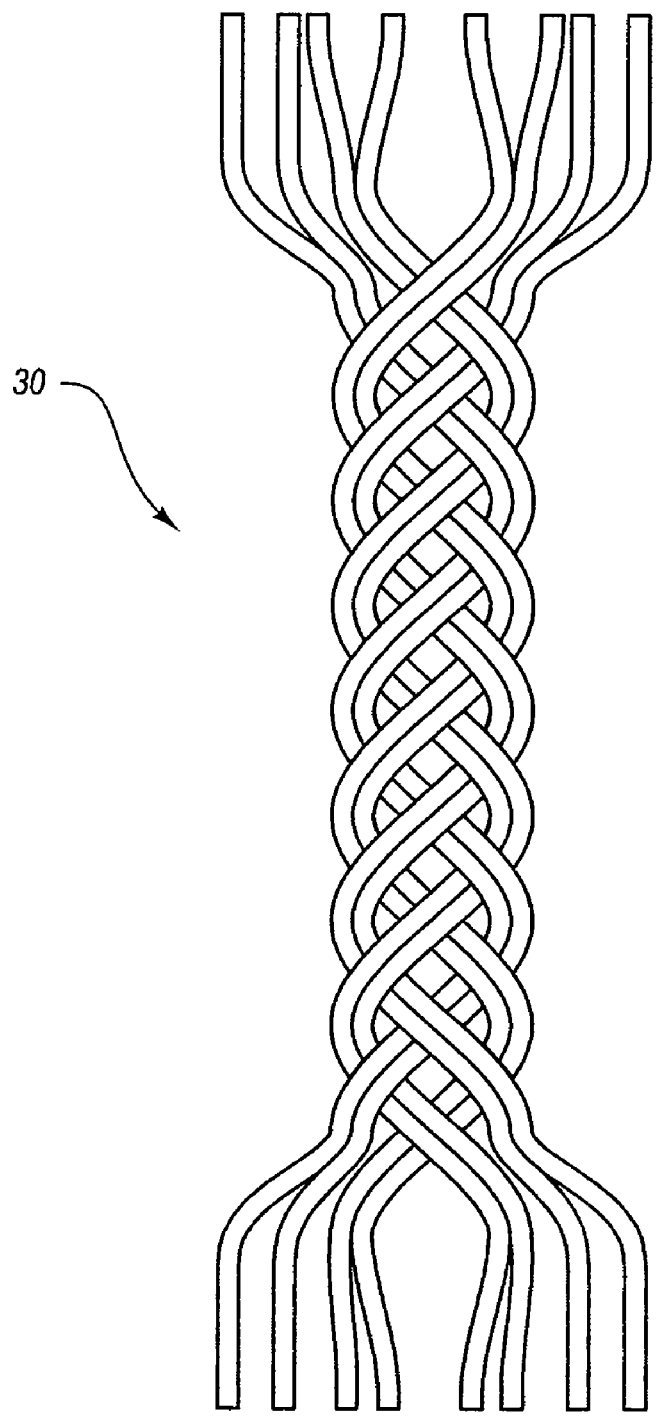
FIG. 1C illustrates an exemplary silk-containing retraction cord having multiple braided strands.

Embodiments of the invention are directed to gingival retraction cords formed from degradation resistant natural fibers so as to have the look, feel and desirable utility of a thin, flexible, and resilient natural fiber cord, while also resisting degradation when pre-impregnated with a corrosive agent, such as an acidic hemostatic agent. Such cords are able to combine the degradation resistance of a man-made fiber, while also having greater liquid absorbance, lightness, flexibility and resilience like a natural fiber cord. This surprising and unexpected combination of features is obtained by manufacturing the retraction cord primarily or exclusively from silk fibers. As used herein, the term "silk" refers to natural protein-based fibers produced by various insects (e.g., the silkworm larvae).

Degradation resistant retraction cords according to the invention comprise at least about 50% silk, preferably at least about 80% silk, more preferably at least about 90% silk, and most preferably at least about 95% silk. According to one embodiment, degradation resistant retraction cords consist essentially, or even entirely, of silk, and are substantially free of man-made fibers such as nylon and polyester. While less preferred, cotton and/or other absorbent materials (e.g., natural fibers) may be included as desired. In addition, other types of degradation-resistant fibers (e.g., nylon and/or polyester) may also be included if desired, though it may be preferable to exclude man-made fibers.

Degradation resistant retraction cords according to the invention can be pre-impregnated with a corrosive agent, such as an acidic hemostatic agent, while maintaining at least about 70% of their tensile strength for a period of time of at least about 7 days, preferably at least about 30 days, more preferably at least about 60 days, and most preferably at least about 90 days.

According to another embodiment, degradation resistant retraction cords are able to maintain at least about 80% of their tensile strength for a period of time of at least about 7 days, preferably at least about 30 days, more preferably at least about 60 days, and most preferably at least about 90 days.

According to yet another embodiment, degradation resistant retraction cords are able to maintain at least about 90% of their tensile strength for a period of time of at least about 7 days, preferably at least about 30 days, more preferably at least about 60 days, and most preferably at least about 90 days.

Although silk retraction cords may absorb less overall liquid than retraction cords made from cotton, they actually absorb more quickly than cotton. However, they are significantly more liquid absorbent than braided retraction cords made from man-made fibers such as nylon and polyester. Moreover, braided silk retraction cords can be thinner and more flexible and resilient compared to braided cords made from man-made fibers. Similar comparisons can be made relative to retraction cords formed by other methods from multiple strands, such as twisted and woven strands. Silk retraction cords are able to exhibit adequate liquid absorbing properties like other natural fibers, but with greatly enhanced long-term strength when pre-impregnated with a corrosive material. Accordingly, silk cords pre-impregnated with a corrosive material are superior to pre-impregnated retraction cords made from natural cotton, on the one hand, and man-made fibers such as nylon or polyester, on the other.

Retraction cords may comprise both silk strands and non-silk strands, so long as the overall composition of the retraction cords is at least about 50% by weight silk, and preferably more as discussed herein. The retraction cords can be formed from two or more strands of pure silk, one or more strands of pure silk together with one or more strands made from other fibers, and/or one or more blended strands formed using a plurality of different types of fibers. The silk fibers and/or strands within the retraction cords of the invention give the retraction cord flexibility, durability and long-term strength integrity when impregnated with a corrosive material. Even if the corrosive agent breaks down or otherwise weakens cotton or other degradable strands or fibers, the inclusion of degradation resistant silk fibers and/or strands help the cord as a whole resist degradation, thereby preserving the overall structural integrity of the cord.

Silk retraction cords according to the invention are advantageously highly elastic and resilient, preferably in both the longitudinal and transverse dimensions. Preferred retraction cords are characterized as being easily stretched along their length and also squeezed or compressed radially. Longitudinal elasticity, or the ability to stretch the retraction cord lengthwise, is beneficial because it avoids the tendency for the packed cord to be dislodged as additional cord is pushed into the sulcus between the tooth and the gingival cuff.

In general, as between twisted-strand or braided-type cords, the use of braided retraction cords has been found to be advantageous over twisted-strand cords because the braided cord better maintains its structural integrity under the force of the dental packing instrument and under the pressure exerted by the surrounding gingival tissue once the cord has been packed into the sulcus.

FIGS. 1A-1C illustrate exemplary silk-containing retraction cords having multiple strands. FIG. 1A depicts an exemplary silk-containing retraction cord 10 having multiple knitted strands. FIG. 1B depicts an exemplary silk-containing retraction cord 20 having multiple twisted strands. FIG. 1C depicts an exemplary silk-containing retraction cord 30 having multiple braided strands.

Retraction cords according to the invention are advantageously sufficiently absorbent so as to allow a liquid active agent to be impregnated within the cords. While not as liquid absorbent as knitted silk cords, braided, twisted-strand and woven retraction cords that are comprised primarily or exclusively of silk are sufficiently liquid absorbent so as to be capable of being pre-impregnated with a liquid active agent. Silk retraction cords are significantly more liquid absorbent compared to retraction cords made from man-made fibers such as nylon or polyester in which the strands are joined together in the same manner.

Hemostatic agents, including astringents and/or other vasoconstrictors, can be pre-impregnated in the retraction cord to control bleeding and/or stiffen gingival tissue. Hemostatic astringents that may be useful in assisting hemostasis include, but are not limited to, aluminum compounds such as potassium aluminum sulfate, aluminum ammonium sulfate, aluminum sulfate, aluminum chlorohydrate, aluminum acetate, aluminum chloride, other water soluble astringent aluminum salts, and mixtures thereof. More preferred hemostatic agents include acidic, but corrosive, iron-based compounds such as ferric salts, including but not limited to ferric sulfate, ferric subsulfate, ferric chloride, and mixtures thereof. An example of an acidic, and therefore corrosive, hemostatic composition that can be applied to a retraction cord is Astringedent®, which is manufactured and sold by Ultradent Products, Inc. Other astringents include permanganates, tannins and zinc chloride. Vasoconstrictors include epinephrine and propylhexedrine.

The active agent(s) may be impregnated into the retraction cord in the form of a liquid that includes the active agent dissolved or dispersed in a volatile solvent, such as water, alcohol and/or ketone, or a non-volatile solvent such as glycerin, propylene glycol, polyethylene glycol and/or polypropylene glycol. The pre-impregnated retraction cords may remain wet or they may be dried, such as by removing a volatile solvent by evaporation to leave the active agent on the retraction cord in the form of a dried residue. Drying the active agent reduces the importance of the cord being more liquid absorbent, like a knitted silk cord, as the dried active agent is able to adhere to the retraction cord regardless of liquid absorbency.

Once made, the pre-impregnated retraction cord may be placed in a moisture resistant container and stored until use. The moisture resistant container protects the pre-impregnated retraction cord from contamination and/or loss of the active agent prior to use. The moisture resistant container is especially beneficial in the case of a pre-impregnated retraction cord that contains a liquid active agent impregnated therein and is designed to remain wet during storage and prior to use. Nevertheless, such containers also help protect dried retraction cords and provide a way to conveniently store and dispense such retraction cords. Pre-impregnated retraction cords manufactured in this manner can be manufactured centrally and distributed to a variety of end users in different locations.

Pre-impregnated retraction cords can be packaged within individual, single use containers, such as foil or plastic packets. Alternatively, a plurality of pre-impregnated retraction cords can be pre-packaged together within a single container, such as a jar or plastic container. A plurality of pre-impregnated retraction cords can be placed in a container having a large removable cover that permits the end user to remove a retraction cord as desired using an appropriate instrument, such as a pair of tweezers. Alternatively, a long length of a pre-impregnated retraction cord can be provided on a spool within a dispensing container, dispensed into desired lengths, and severed to yield individual retraction cords as needed. The length of pre-impregnated retraction cord can be severed using cutting means known in the art, such as scissors or a knife, or by a cutting tool permanently attached to the dispensing container. The length of pre-impregnated retraction cord can also be perforated or otherwise divided into discrete weakly attached segments that are easily separated after being dispensed from the dispensing container.

Figure 2A:
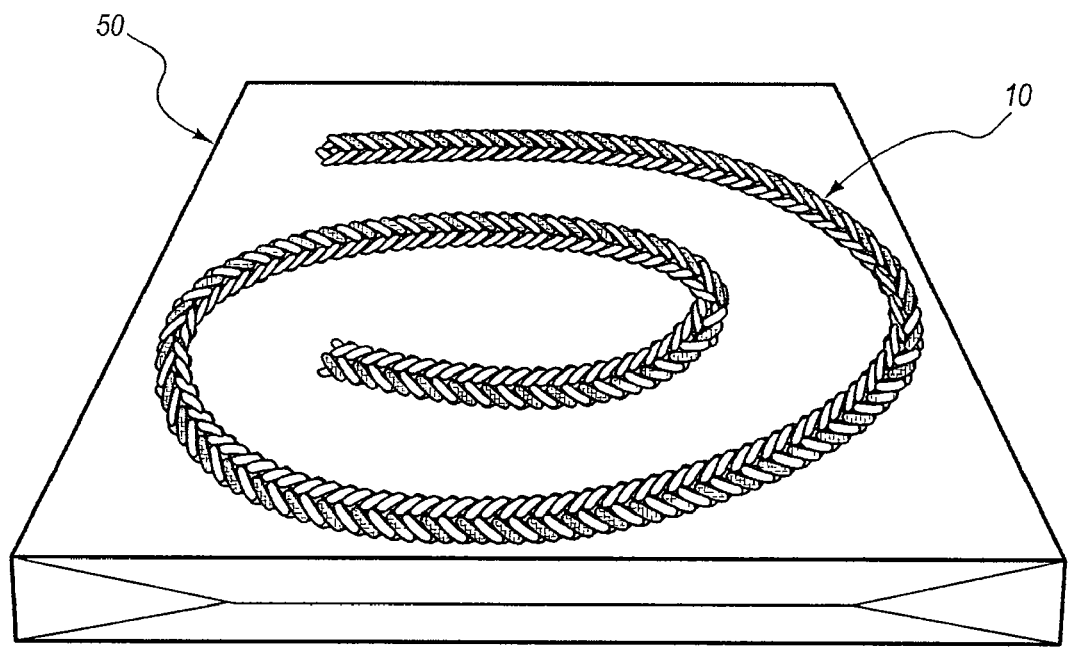
FIG. 2A illustrates an exemplary silk-containing retraction cord having multiple knitted strands within a packaging container.
Figure 2B:
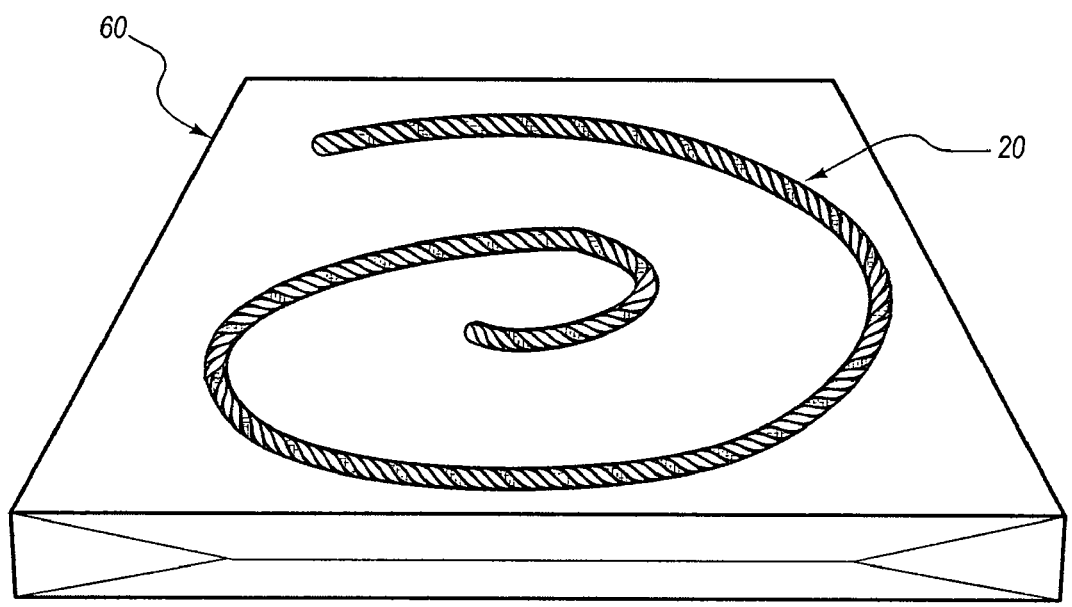
FIG. 2B illustrates an exemplary silk-containing retraction cord having multiple twisted strands within a packaging container.
Figure 2C:
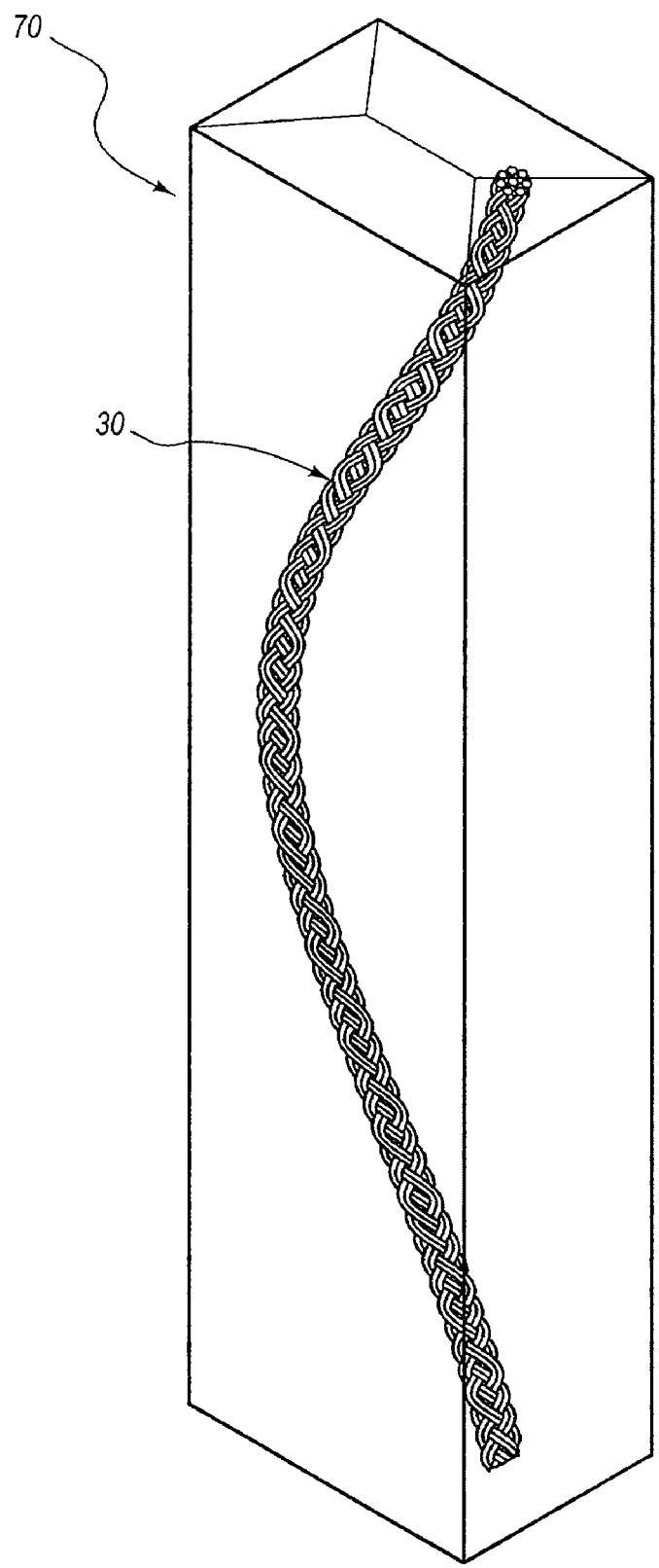
FIG. 2C illustrates an exemplary silk-containing retraction cord having multiple braided strands within a packaging container.

FIGS. 2A-2C illustrate exemplary silk-containing retraction cords within a packaging container. FIG. 2A depicts an exemplary silk-containing retraction cord 10 having multiple knitted strands within a packaging container 50. FIG. 2B illustrates an exemplary silk-containing retraction cord 20 having multiple twisted strands within a packaging container 60. FIG. 2C illustrates an exemplary silk-containing retraction cord 30 having multiple braided strands within a packaging container 70.

In use, one or more retraction cords that have been impregnated with an active agent are placed in the sulcus between the patient's tooth and gingival using packing tools known in the art. During use, silk retraction cords provide an active agent to the sulcus, such as a hemostatic agent. They may also be able to absorb blood or other fluid if not already saturated with liquid.

Comparative Example

In order to demonstrate the surprising and unexpected strength of silk retraction cords compared to conventional cotton cords when pre-impregnated with a corrosive agent, a commercially available cotton retraction cord and a similarly manufactured silk retraction were pre-impregnated with a commercially available hemostatic composition. The cotton retraction cord used in the test was an Ultradpak® Cotton Cord made by Ultradent Products, Inc., and the silk cord was prepared in a similar manner at Ultradent Products, Inc. The hemostatic agent used in the test was Astringedent®, which is also made by Ultradent Products, Inc.

The cotton and silk retraction cords were each impregnated with Astringedent® and left to dry for 36 hours at room temperature. After 36 hours the cords were inspected and slightly tugged to see if there was any elasticity or strength left in the cords. The silk cord retained most of its tensile strength and elasticity. However, the cotton cord had lost most of its strength and broke with the slightest tug. It also had a brittle appearance. As such, the pre-impregnated cotton cord was unsuitable for use as a gingival retraction cord, as it lacked sufficient strength to be packed into the sulcus between a tooth and gingival tissue. This is consistent with a previous test, in which a cotton cord impregnated with Astringedent® became friable and lost essentially all of its original tensile strength over time.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A pre-packaged, chemically impregnated gingival retraction cord that is resistant to degradation by corrosive agents over time, comprising:
   a gingival retraction cord comprising two or more strands that are joined together so as to be deformable and liquid absorbent, wherein the retraction cord is silk-containing;
   a corrosive agent impregnated within the retraction cord, wherein the retraction cord resists degradation by the corrosive agent so as to maintain at least about 70% of its tensile strength over a time period of at least about 7 days; and
   a packaging container within which the retraction cord is stored prior to use.

2. A pre-packaged, chemically impregnated gingival retraction cord as in claim 1, wherein the retraction cord comprises at least about 50% silk.

3. A pre-packaged, chemically impregnated gingival retraction cord as in claim 1, wherein the retraction cord comprises at least about 80% silk.

4. A pre-packaged, chemically impregnated gingival retraction cord as in claim 1, wherein the retraction cord comprises at least about 90% silk.

5. A pre-packaged, chemically impregnated gingival retraction cord as in claim 1, wherein the retraction cord consists essentially of silk.

6. A pre-packaged, chemically impregnated gingival retraction cord as in claim 1, wherein the retraction cord is substantially free of man-made fibers.

7. A pre-packaged, chemically impregnated gingival retraction cord as in claim 1, wherein the retraction cord resists degradation by the corrosive agent so as to maintain at least about 70% of its tensile strength for at least about 30 days.

8. A pre-packaged, chemically impregnated gingival retraction cord as in claim 1, wherein the retraction cord resists degradation by the corrosive agent so as to maintain at least about 70% of its tensile strength for at least about 60 days.

9. A pre-packaged, chemically impregnated gingival retraction cord as in claim 1, wherein the two or more fibers are braided, twisted or woven.

10. A pre-packaged, chemically impregnated gingival retraction cord as in claim 1, wherein the corrosive agent comprises a hemostatic agent.

11. A pre-packaged, chemically impregnated gingival retraction cord as in claim 10, wherein the hemostatic agent is comprised of an acidic iron based salt.

12. A pre-packaged, chemically impregnated gingival retraction cord as in claim 1, wherein the corrosive agent is a liquid or dried residue.

13. A pre-packaged, chemically impregnated gingival retraction cord as in claim 1, wherein the retraction cord further comprises a non-corrosive vasoconstrictor.

14. A pre-packaged, chemically impregnated gingival retraction cord as in claim 13, wherein the non-corrosive vasoconstrictor comprises at least one of epinephrine or propylhexedrine.

15. A chemically impregnated gingival retraction cord that is resistant to degradation by corrosive agents over time, comprising:
   a gingival retraction cord comprising two or more strands that are joined together so as to be deformable and liquid absorbent, wherein the retraction cord is silk-containing;
   a corrosive agent impregnated within the retraction cord, the corrosive agent comprising a dried residue,
   wherein the retraction cord resists degradation by the corrosive agent so as to maintain at least about 70% of its tensile strength over a time period of at least about 7 days.

16. A chemically impregnated gingival retraction cord as in claim 15, wherein the retraction cord comprises at least about 50% silk.

17. A chemically impregnated gingival retraction cord as in claim 15, wherein the retraction cord consists essentially of silk and other natural fibers and is free of man-made fibers.

18. A chemically impregnated gingival retraction cord as in claim 15, wherein the retraction cord resists degradation by the corrosive agent so as to maintain at least about 70% of its tensile strength for at least about 30 days.

19. A chemically impregnated gingival retraction cord as in claim 15, wherein the two or more fibers are braided, twisted or woven.

20. A chemically impregnated gingival retraction cord as in claim 15, wherein the retraction cord further comprises a non-corrosive vasoconstrictor.

21. A chemically impregnated gingival retraction cord as in claim 20, wherein the non-corrosive vasoconstrictor comprises at least one of epinephrine or propylhexedrine.

22. A chemically pre-impregnated gingival retraction cord that is resistant to degradation by corrosive agents over time, comprising:
   a gingival retraction cord comprising two or more strands that are joined together so as to be deformable and liquid absorbent, wherein the retraction cord is silk-containing;
   a corrosive liquid material that has been impregnated into and has remained in contact with the retraction cord for a time period of at least about 30 days,
   wherein the retraction cord resists degradation by the corrosive liquid material so as to maintain at least about 70% of its tensile strength over the time period of at least about 30 days.

23. A chemically pre-impregnated gingival retraction cord as in claim 22, wherein the retraction cord further comprises a non-corrosive vasoconstrictor.

24. A chemically pre-impregnated gingival retraction cord as in claim 23, wherein the non-corrosive vasoconstrictor comprises at least one of epinephrine or propylhexedrine.

25. A method of manufacturing a pre-packaged, chemically impregnated gingival retraction cord that is resistant to degradation by corrosive agents over time, comprising:
   providing a gingival retraction cord comprising two or more strands that are joined together so as to be deformable and liquid absorbent, wherein the retraction cord is silk-containing;
   impregnating a corrosive agent into the retraction cord to form a chemically impregnated retraction cord; and
   placing the chemically impregnated retraction cord into a packaging container, wherein the retraction cord resists degradation by the corrosive agent so as to maintain at least about 70% of its tensile strength over a time period of at least about 7 days.

26. A method as in claim 25, wherein the corrosive agent is initially dissolved or dispersed in a liquid solvent prior to being impregnated into the retraction cord.

27. A method as in claim 26, after impregnating the corrosive agent into the retraction cord, the method further comprising removing the liquid solvent by evaporation in order to convert the corrosive agent into a dried residue.

28. A method as in claim 25, further applying a non-corrosive vasoconstrictor to the retraction cord.

29. A method as in claim 28, wherein the non-corrosive vasoconstrictor comprises at least one of epinephrine or propylhexedrine.

30. A method of manufacturing a chemically impregnated gingival retraction cord that is resistant to degradation by corrosive agents over time, comprising:

providing a gingival retraction cord comprising two or more strands that are joined together so as to be deformable and liquid absorbent, wherein the retraction cord is silk-containing;

impregnating a corrosive agent into the retraction cord to form a chemically impregnated retraction cord, wherein the corrosive agent is initially dissolved or dispersed in a liquid solvent prior to impregnation into the retraction cord; and removing the solvent by evaporation in order to convert the corrosive agent into a dried residue, wherein the retraction cord resists degradation by the active agent so as to maintain at least about 70% of its tensile strength over a time period of at least about 7 days.

31. A method as in claim 30, further applying a non-corrosive vasoconstrictor to the retraction cord.

32. A method as in claim 31, wherein the non-corrosive vasoconstrictor comprises at least one of epinephrine or propylhexedrine.

* * * * *

UNITED STATES PATENT AND TRADEMARK OFFICE
CERTIFICATE OF CORRECTION

| | | |
|---|---|---|
| PATENT NO. | : 7,922,487 B2 | Page 1 of 1 |
| APPLICATION NO. | : 12/135756 | |
| DATED | : April 12, 2011 | |
| INVENTOR(S) | : Fischer | |

It is certified that error appears in the above-identified patent and that said Letters Patent is hereby corrected as shown below:

Column 3
Line 13, change "exclusive" to --exclusively--

Column 6
Line 37, change "gingival" to --gingiva--
Line 51, change "Ultradpak®" to --Ultrapak®--

Signed and Sealed this
Ninth Day of August, 2011

David J. Kappos
*Director of the United States Patent and Trademark Office*